United States Patent [19]

Leonard

[11] Patent Number: 4,748,024

[45] Date of Patent: May 31, 1988

[54] FLASH FLOW FUSED MEDICINAL IMPLANTS

[75] Inventor: Robert J. Leonard, Lynnfield, Mass.

[73] Assignee: Endocon, Inc., Boston, Mass.

[21] Appl. No.: 35,379

[22] Filed: Apr. 6, 1987

[51] Int. Cl.[4] .............................................. A61K 31/56
[52] U.S. Cl. .................................. 424/489; 424/502; 514/178
[58] Field of Search ...................... 424/482, 489, 502; 514/178

[56] References Cited

U.S. PATENT DOCUMENTS

| | | | |
|---|---|---|---|
| 4,244,949 | 1/1981 | Gupta | 514/178 |
| 4,349,530 | 9/1982 | Roger | 424/489 X |
| 4,396,630 | 8/1983 | Ricdl et al. | 424/502 X |

*Primary Examiner*—Michael R. Lusignan
*Attorney, Agent, or Firm*—Wolf, Greenfield & Sacks

[57] ABSTRACT

A process and a device for preparing a fused pellet from nonethindrone and cholesterol are provided. Conditions are applied to the pelleting material to melt the material uniformly such that the phase transition of all of the material occurs approximately simultaneously. The material is removed from the melting conditions immediately upon the melting of the material and the material is subjected immediately to cooling conditions.

20 Claims, 2 Drawing Sheets

FLASH FLOW FUSED MEDICINAL IMPLANTS

BACKGROUND OF THE INVENTION

This invention relates in general to a process for making fused medicinal implants, preferably in the form of cylindrical pellets for the subcutaneous implantation and delivery of drugs and in particular to a process for making a fused implant for fertility control and certain endocrinologically mediated disorders.

It has become widely acknowledged that standard oral and parenteral (intravenous or intramuscular) forms of drug delivery represent relatively inefficient means of administering therapeutic pharmaceuticals, due to considerable drawbacks associated with conventional drug-delivery methods. These drawbacks arise from the way in which standard dosage forms of pharmacologically active compounds are absorbed into the body, circulated through the blood stream, cleared and excreted. Conventional routes of administration generally require the administration of far more of a drug than is therapeutically warranted so that there will be adequate blood levels of drug between doses ("spiking"). Moreover, there are many therapeutically vital substances which present a narrow ratio of efficacy to toxicity that do not, therefore, lend themselves to traditional routes of administration. Additionally, drugs that require daily compliance with a multiple-dose regimen on the part of the patient pose a major problem in the management of the chronically ill, elderly, those with emotional disorders, and people whose lifestyles do not comfortably accommodate regular routine. The lists of conditions requiring such regimens is extensive and includes: diabetes; psychiatric diseases; cancer; and coronary artery disease, to name only a few.

In recent years, various types of novel sustained release drug-delivery systems have begun to receive widespread attention. Such drug-delivery systems include certain implantable devices which slowly dissolve or somehow release drugs while under the patient's skin. Implants are particularly effective and economical forms of treatment because a single administration of such a product can deliver, over a long period of time (a year or more), adequate therapeutic serum levels of a drug without reliance on patient compliance, frequent clinic visits and while avoiding over medication due to "spiking". Known implantable systems have drawbacks. Some are not long-acting enough; some have what are called poor kinetics, which cause them to release drug in less even and predictable amounts over time; some are too long in duration; some are irreversible (impossible to discontinue, once begun); and others require surgical removal when the system is depleted of drug.

Implantable systems for fertility control, as well as for other clinical applications, have long been sought as an alternative to oral preparations of steroids. This approach is particularly attractive to developing nations, where national health-care networks are at a disadvantage in reaching a population which is demographically and educationally ill controlled. Moreover, significant potential health problems associated with the use of certain steroids have raised many questions as to the wisdom of prescribing steroids in the amounts required for effective oral delivery. A progestogen—only implant for fertility control, the Silastic implant—NORPLANT ®—has been extremely well accepted in fertility control trials throughout the world despite the cumbersome nature of multiple, one-inch or longer rods that must be surgically implanted and removed when depleted. The subject of the current invention includes a process which yields a bioerodable fused pellet coupling active and nonactive ingredients and prepared for subdermal implantation, which reduces the disadvantages of the known long term implantable drug delivery systems.

It is known that bioabsorbable implants can be made by various methods and utilizing various materials. Several methods have been practiced with steroid drugs. For example, a bioabsorbable implant can be made by tightly compressing powdered steroid. An improved implant results from compressing a combination of a nonactive biocompatible binder and the steroid into a pellet which pellet releases steroid more slowly and more uniformly than the pure steroid pellets.

An important improvement over the compression process for making pellets which results in even longer and more constant dissolution rates, is a method of melting a drug together with a sufficient amount of a nonactive lipoid carrier resulting, when cooled, in a "fused" pellet. The superior kinetics and release rates are believed to be due to the final integral crystal lattice produced from the starting materials. It has been suggested that such a "fused" implant of a sex steroid uniformly dispersed with a suitable lipoid carrier may provide a convenient, safe and effective form of long-term fertility control in mammals. Specifically, a precise intimate mixture of the starting materials in their micronized crystalline form, as supplied by the manufacturer, is heated according to the published melting points of either the active ingredient or the carrier or to a eutectic point of the two where a phase change occurs and an isotropic liquid (perfectly clear melt) is achieved. At this point, the materials are allowed to cool or are quenched whereupon the melt hardens through recrystallization into the final, integral "fused" pellet. Such fused implants, however, have proven unsuitable for a variety of reasons, largely related to the manufacturing processes used which are not easily reproducible. The background of such fused implants is discussed in greater detail in U.S. Pat. No. 4,244,949 (Gupta).

The methods suggested by Gupta and others for making such a fused implant rely heavily upon manual skills, have a very low yield of effective final product when performed by anyone unpracticed in the procedure and do not lend themselves to automated mass production techniques. In particular, the best of the prior art methods known to applicant requires pre measuring and dispensing into very small vessels minute amounts of active ingredient and carrier. The material must be gradually heated within a vessel while gently applying a continuous pressure, with steel rods, at each end of the vessel until a clear liquid phase is determined by eye. Then the melted material is removed from the heat source and allowed to cool. This human-dependent process not only is inefficient, but is more a craft than a practicable method capable of being reproduced consistently. This is especially important as it relates to the Good Manufacturing Practices promulgated by the FDA as necessary for the commercial approval of any drug.

The requirement of delicate manipulations and skilled judgment on the part of an individual introduces a potential for error with the making of each pellet. The duration of which the material is exposed to temperature is not adequately controlled according to prior art methods and the material may be overheated, causing de-ethynylation of the active ingredient. This effect has been misunderstood in previous art resulting in the presumption that oxidation—an atmospheric effect—was the cause of degradation of the final product. Therefore, this art sought to avoid open air or atmosphere melts and introduced manufacturing steps that actually created a greater likelihood of both degradation due to duration of heat exposure as well as the "capturing" of gases within the final product. Moreover, cumbersome procedural steps and apparatus were introduced to avoid open air melts.

The pressure applied to the melt also is not quantitatively controlled according to these prior art methods. Also, the integrity of the final crystal of the fused pellet may be adversely affected by transverse fractures and friability as the crystal forms when the melt is manually removed from the heat source. Pre-measuring and dispensing of the ingredients by hand into the vessels introduces the potential for error and contamination. Moreover, this practice necessitates an undesirable degree of human exposure to steroids in powder form, demanding the strictest controls according to the rules promulgated by the FDA. Also, certain of the prior art methods require purification of the starting materials by recrystallizing them using various solvents, nitrogen chambers and dessicators in order to assure that gases or moisture were eliminated from the crystals.

Applicant's invention overcomes these and other shortcomings. Applicant provides a process for forming a fused pellet that does not require the skilled manipulation and human judgment previously enumerated and that is capable of automation and suitable for large scale commercial production. Applicant also provides a process for forming a fused implant that does not result in de-ethynylation or other degradation products of the starting materials. Applicant's process for forming a fused pellet further does not require an oxygen free environment and does not "trap" air or gases, but rather allows the free evaporation of impurities which otherwise might be collected within the tortuous geometry of the individual crystals of the starting materials.

Another object of the invention is to provide a process for dispensing the intimate mixture in precise relative amounts in an automated fashion where the active ingredient comprises over 50% of the final drug product.

SUMMARY OF THE INVENTION

A process for preparing a fused pellet from certain starting materials is provided. Conditions are applied to the materials to melt the mixture uniformly such that the phase transition of virtually all of the material occurs simultaneously, preferably over a range of not more than about 10 seconds. The material is then motivated from the heat source, preferably through a combination of the inherent properties of the clear melt and a mechanical force, such as a slight vacuum.

To accomplish a quick and uniform melt, a flash flow method and device are provided. First, a paste may be made from an intimate mixture of the micronized crystalline form of the starting materials as supplied by the manufacturer, the active ingredient being present in at least an amount of 50% of the total material. A thin layer of this paste then is applied to a nonstick surface, such as a fluorocarbon like Teflon ®, which surface, in turn, is affixed to a thin, heat-conductive metallic wall. The thin layer of paste, nonstick surface and heat conductive wall are oriented at an angle, preferably inclined at least about 45° to horizontal. A heat source then is applied to the surface of the heat conductive wall opposite the surface layered with the nonstick surface and paste. The heat is applied uniformly across this entire surface at a temperature sufficient to uniformly melt the layer or "skin" of material such that the phase transition of all of the material occurs approximately simultaneously, and preferably in 10 seconds or less. Upon the phase transition, the isotropic liquid beads upon the nonstick surface and runs off of this inclined surface. The material is collected as it runs off the surface and is allowed to cool into a fused pellet, preferably within a fluorocarbon chamber of appropriate size and shape.

In one significant case, the fused pellet is made of an antifertility steroid molecule such as nonethindrone (NET) and a lipoid carrier such as pure cholesterol. Such a fused pellet may be used as an implant for fertility control in humans and animals. Other applications may include a variety of other drugs for the management of various clinical conditions.

DETAILED DESCRIPTION OF THE DRAWINGS

Figure 1:
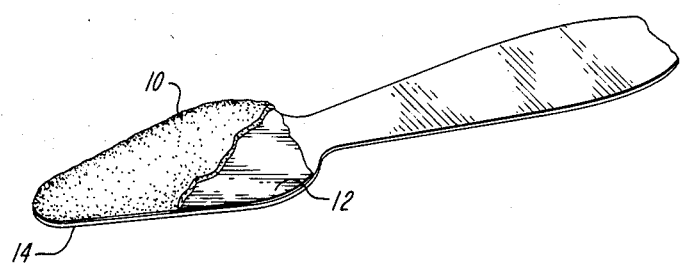
FIG. 1 is a schematic representation showing the material spread in a thin layer prior to fusion.

Applicant's invention allows the formation of a fused pellet containing steroid and cholesterol in relative amounts of at least 50% steroid. There is no de-ethynylation or other degradation of the starting materials and air is not entrapped in the pellet. To accomplish this, applicant applies a thin layer or "skin" of a mixture of the starting materials to a thin layer of conductive metal. Preferably the surface upon which the skin is applied is coated with a nonstick material such as Teflon ®. When a heat source well above the melting temperature of the starting materials is applied to the underside of the conductive metal, the starting materials mixture reaches a clear melt state in less than 10 seconds, beading like mercury and exhibiting excellent flow characteristics when inclined at an angle of about 45° to horizontal. When so inclined, the melted material is motivated to leave the area of the heat source the moment it reaches the clear melt stage. This eliminates the risk of degradation posed by overexposure to heat, which is a persistent problem of the prior art methods for preparing fused pellets. Moreover, since the procedure is atmospheric, there is no capturing of air.

The clear, nondegraded material will flow from the inclined surface and may be collected into a vessel having a nonstick surface of appropriate size and shape for forming a pellet. Collection and pellet formation may be aided by the application of a slight vacuum from beneath the collection vessel utilizing, for example, a Teflon ® filter or a Gortex membrane. The collected material further may be drawn from above or below into a pellet forming chamber of appropriate size and shape by a conventional piston beginning with a plunger in the closed position.

An accurate dispensing of the starting materials may be achieved by forming a paste made from the powdered mixture of starting materials and a liquid such as ethyl alcohol, which alcohol may be dried out of the starting materials after dispensing, utilizing, for example, a standard vacuum oven. By forming a paste, the material can be dispensed accurately from a standard, automated device such as a micropipetter. The paste may be manufactured to have the flow characteristics of ordinary toothpaste.

The formation of the paste clearly overcomes problems in the prior art. Where drugs such as steroids are concerned, anything but a precise dosage could either be ineffective or harmful to the user. It has been represented to applicant that standard pharmaceutical dispensing machinery for dispensing powder does not dispense the very small quantities of powder required for the individual pellets of the invention with sufficient accuracy. This is especially true when the active ingredient comprises over 50% of the total pellet volume. Therefore, according to the prior art, the materials must be measured or carefully aliquoted separately for each pellet. By forming a paste, applicant has discovered that the precise relative amounts of steroid and carrier are maintained homogeneously throughout the paste and individual manual measurements are thus obviated. The paste also facilitates forming the thin "skin" of pelleting materials according to the invention.

The liquid agents used to formulate the paste may be ethyl alcohol or any volatile organic solvent which can be evaporated completely prior to applicant's flash flow process and which when combined with the starting materials yield suitable flow characteristics. The liquid agent should be of a nature that promotes the quick drying of the paste once the paste is applied as a skin. The liquid agent, of course, should not be of a nature which affects the activity of the active agent in the pellet.

Figure 2:
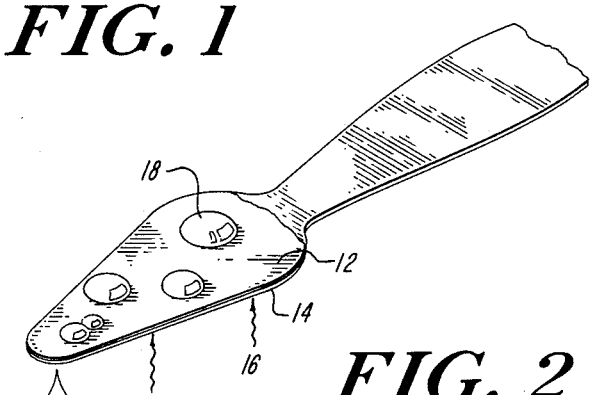
FIG. 2 is a schematic representation showing the material after the application of heat.

FIGS. 1 and 2 are a schematic representation illustrating the basic principles of applicant's invention. A thin skin 10 of starting materials, less than 1 mm thick, was spread on a Teflon ® surface 12 layered on a heat conductive metal base 14. Heat well in excess of the melting temperature of the starting materials, indicated by arrows 16, was then applied to the underside of the heat conductive metal base 14 which was inclined at an angle about 45° to horizontal. In approximately 3 to 5 seconds, the skin 10 melted into a clear liquid 18 which immediately beaded and ran down the Teflon ® surface away from the heat source as shown in FIG. 2. The beads of the clear liquid 18 were collected in a vessel 20 away from the heat source. The clear liquid 18 then was allowed to cool.

Figure 3:
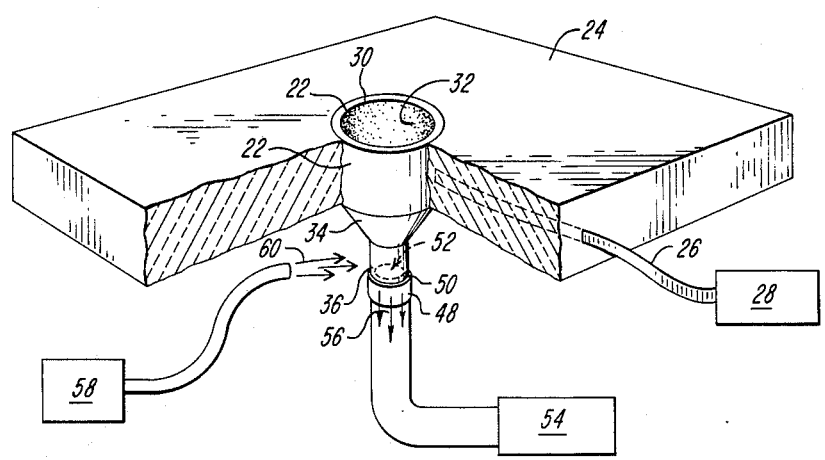
FIG. 3 is a schematic representation showing applicant's preferred device for carrying out the invention.
Figure 4:
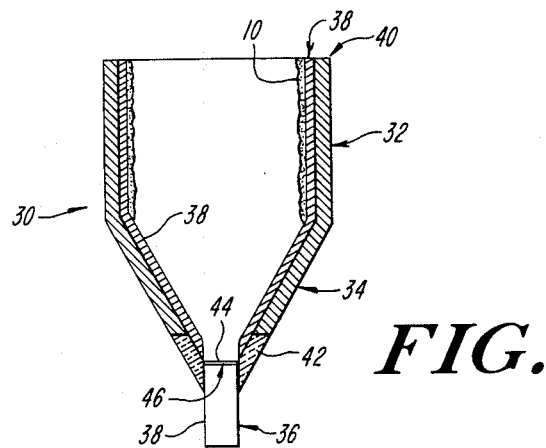
FIG. 4 is a schematic representation of a component device shown in FIG. 3.

FIGS. 3 and 4 illustrate a device for carrying out applicant's process. A metal heating collar 22 is contained in an insulative ceramic block 24. The metal heating collar 22 is connected via an energy conduit 26 to an energy source 28 for heating the metal heating collar 22. The metal heating collar 22 receives a melt cup 30. The melt cup 30 has upper cylindrical walls 32 and middle conical walls 34 decreasing in diameter until they meet lower cylindrical walls 36. The heating collar 22 and melt cup 30 are sized such that the collar mates with and contacts the upper cylindrical walls 32 of the melt cup. The conical walls 34 and cylindrical walls 36 of the melt cup extend below and do not contact the heating collar 22.

A preferred embodiment of the melt cup 30 is shown in cross section in FIG. 4. The upper cylindrical, middle conical and lower cylindrical walls 32, 34, 36 are formed at least in part of a nonstick wall 38 preferably made from Teflon ®. An outer, heat conductive metal wall 40, preferably made of aluminum or stainless steel, surrounds and contacts the upper cylindrical walls 32 and an upper portion of the middle conical walls 34. An outer insulative ceramic wall 42 surrounds and contacts the lower portion of the middle conical walls. This outer insulative ceramic wall 42 acts as a barrier to the transfer of heat from the outer heat-conductive wall 40 to the lower cylindrical walls 36 of the melt cup. Preferably the melt cup 30 has a horizontal wall 44 separating the space defined by the middle conical walls 34 and the lower space defined by the cylindrical walls 36. The horizontal wall 44 has a microbore 46 through which the melted clear liquid may be drawn. The thin skin 10 of starting materials is layered on the nonstick surface of the upper cylindrical walls 32 of the melt cup 30.

Referring back to FIG. 3, the preferred device includes a sealing member 48 for closing off the open end of the lower cylindrical walls 36. The sealing member includes a plug 50 sized to sealably fit into the opening of the lower cylindrical walls 36. Preferably the top surface of the plug 50 is a Teflon ® or Gortex ® filter membrane 52. This filter membrane 52 communicates with passages (not shown) which in turn communicate with a vacuum 54, such that a force indicated by arrows 56 may be applied to pull the melted liquid through the microbore and into the space defined by the lower cylindrical walls 36. This vacuum force aids in collecting the melted liquid and acts to eliminate any bubbles that may be trapped within or below the melted liquid as it collects. The preferred embodiment also includes a cooling device 58 for providing a cooling force indicated by arrows 60 to the lower cylindrical walls 36 of the melt cup 30.

In operation, the melt cup 30 is coated with the skin 10. The melt cup 30 then is inserted into the heating collar 22. The skin then will melt with the clear melt beading and immediately flowing away from the heat to the horizontal wall 44 of the melt cup. The vacuum force then pulls the clear liquid through the microbore into the chamber formed by the horizontal wall 44, plug 50 and the lower cylindrical walls 36 of the melt cup 30. Preferably, the chamber is sized and the amount of pelleting material is selected such that a small excess of melted clear liquid remains above the horizontal wall 44 in communication with the chamber through the microbore 46. Applicant has discovered that if the material is allowed to cool in the absence of the horizontal wall, a hollow may form centrally of the exposed face of the material. By introducing the horizontal wall with a microbore and using an excess of material communicating with the chamber through the microbore, the hollow does not occur when the material cools. An excess amount of material is not required if the horizontal wall does not contain a microbore and is introduced to cover the material without trapping air only after all the melt has entered the chamber. The clear liquid then cools in this chamber, forming the pellet. The pellet is subsequently removed from the chamber.

Figure 5:
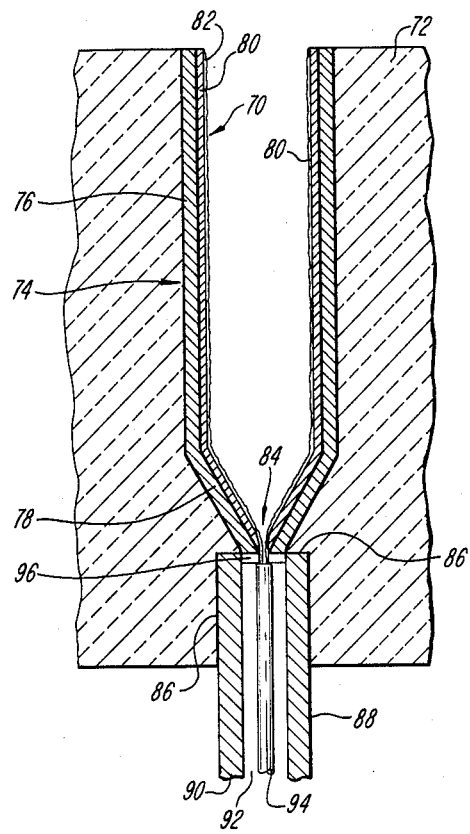
FIG. 5 is a schematic cross sectional representation of another embodiment of a device for carrying out the invention.

Another embodiment of a device of the invention is shown in cross section in FIG. 5. In this embodiment, the melt cup 70 is received completely within the ceramic block 72 rather than extending through the ceramic block as in the previous embodiment. A heating collar 74 is contained in the ceramic block 72. The heating collar 74 has upper cylindrical walls 76 and lower conical walls 78 decreasing in diameter. The melt cup 70 has mating walls 80 sized to be received and contact the walls 76, 78 of the heating collar 74. The inside surface 82 of the melt cup 70 is coated with a nonstick surface such as Teflon ®.

The conical portion of the mating walls 80 of the melt cup 70 end in an exit port 84 opening into a chamber defined by the chamber-forming walls 86 of the ceramic block 72. The chamber formed by the chamber-forming walls 84 is sized to receive a pellet-forming cylinder 88. The pellet-forming cylinder 88 has outer walls 90 and a central bore 92 through which a plunger 94 may be passed.

In operation, the pellet-forming cylinder 88 is inserted into the chamber defined by the channel-forming walls 86 of the ceramic block 72. The plunger 94 is moved to a closed position such that it closes off the exit port 84 of the melt cup 70. The beads of melted pelleting material will run down the walls of the melt cup 70 and collect forming a pool above the exit port 84 of the melt cup. The plunger then is withdrawn pulling the clear liquid through the exit port 82 of the melt cup into the bore 92 of the pellet forming cylinder. The liquid is allowed to cool into a pellet within this bore. Preferably, the exit port 84 has a substantially smaller diameter than the diameter of the bore 92. In this manner the desired amount of liquid is drawn into the bore 92 with the excess remaining in the melt cup 70. Once the liquid has cooled and hardened the pellet-forming cylinder is withdrawn from the chamber with the pellet breaking away from the excess of material remaining in the melt cup. The pellet then may be released from the chamber by moving the plunger 94.

Although applicant does not wish to be bound by any particular theory of applicant's invention, applicant believes that the pellet forms without degradation because the melt is motivated from the heat source immediately upon melting and is not overexposed to heat. Applicant has found that degradation will occur if a melt of starting materials is maintained at about the melt temperature for any extended period of time. Accordingly, applicant believes that very high flash temperatures are possible so long as the melt is not maintained at or above the melting temperature but rather is immediately cooled.

Applicant believes that some of the shortcomings of the prior art are due to overexposing the melt to the melting temperatures. Following the methods of the prior art, the pelleting materials do not melt uniformly but rather melt about the periphery first with melting progressing slowly toward the central region of the packed material. Ostensibly, the material melting first is exposed to heat for an extended period of time until all of the material melts. According to applicant's preferred embodiment, the pelleting materials are in the form of a skin that is thin enough such that the materials will melt approximately simultaneously, in not more than about 10 seconds. The material is then motivated immediately from the source of heat. In this manner, applicant prevents degradation of the pelleting materials. Preferably the skin is less than about 1 mm in thickness. According to applicant's process, the starting materials may be exposed to flash temperatures more than twice those indicated in the prior art.

It also is preferable that the conductive wall to which the heat is applied is thin enough such that the material is not slowly heated, but rather is exposed to high temperatures immediately. To insure that the melt is uniform or instantly isotropic, the heat source should completely surround the material to prevent spot melting. There may be no practical limit to the flash temperatures to which the conductive walls are exposed. Higher temperatures, in fact, may expose the material to heat for a shorter time and the material may, therefore, be less likely to degrade.

While applicant has described achieving desirable results using a skin of material, it may be that the same results can be achieved by exposing the pelleting materials to other conditions. For example, a packed pellet of the starting materials possibly may be exposed to microwave conditions to achieve the uniform melt. The critical parameters are that the pelleting materials are exposed to the melting conditions for the shortest time possible, that the phase transition from solid to liquid occurs approximately simultaneously for all the material and that the melted material is immediately subjected to cooling conditions when melting occurs. The rate at which the melt is cooled may affect the integrity of the pellet.

Applicant has discovered that the rate at which the clear melt cools also affects the structure and the kinetics of release of the pellet. In particular, noneutectic melts appear to crystallize as eutectics initially with the surplus of material spot crystallizing throughout the eutectic lattice. These points of spot crystallization appear to weaken the overall structure of the crystallized pellet. By subjecting the noneutectic melt to quenching or rapid cooling conditions, the surplus material does not appear to crystallize properly, but rather appears to solidify amorphously throughout the eutectic lattice. The resulting structure appears to be more stable and may have better release kinetics than a eutectic melt. Therefore, it appears desirable to use a noneutectic mixture and apply rapid cooling conditions to the mixture as soon as the melt is collected into a pellet forming chamber.

A partially fused pellet also may be possible according to the invention. In a partially fused pellet, the starting materials are exposed to conditions such that only the carrier material melts, with the active material remaining as a solid dispersion throughout the melt. When the partial melt solidifies a pellet having clinically desirable drug release kinetics may result. Such partially fused pellets may be useful for the delivery of drugs which are either not steroids or do not have crystalline properties.

EXAMPLE 1

85 grams of pharmaceutical grade, micronized nonethindrone (provided by Diosynth, Inc. of Chicago, Ill.) and 15 grams of pure, pharmaceutical grade cholesterol (provided by ICN Pharmaceuticals of Covina, Calif.) were intimately mixed and ground in a mortar and pestle. Thirty-five milligrams of this mixture then were spread on a Teflon ® coated steel spatula. The stainless steel spatula was approximately 20 mm in length and 10 mm in width and was covered uniformly with a fine layer of Teflon ® tape. The skin applied was about 0.5 mm in thickness. The nonTeflon ® coated side of the spatula then was brought in contact with a hot plate which was heated to approximately 500° F. A clear melt resulted which beaded up like mercury and rolled off the surface of the spatula when the spatula was held at an angle about 45° to horizontal. The spatula was contacted with hot plate for less than 10 seconds. Upon cooling, the "fused" material was pure white, implying the lack of degradation products. The absence of any yellow indicated that there was no de-ethynylation of the nonethindrone. The pellet was resilient and could be filed and formed with a very gentle abrasive action. Based on a visual light microscopy of the fracture surface, the pellet appeared to have the same characteristics of the very best of those made according to the prior art methods.

EXAMPLE 2

The same procedure as set forth in Example 1 was followed except that the starting materials were applied to the Teflon ® coated spatula in the form of a paste. Two grams of the mixture of nonethindrone and cholesterol were mixed with 2 ml of 100% laboratory grade ethyl alcohol using a spatula to form a paste. The paste was spread onto the spatula in a thickness of about 0.5 mm and allowed to dry in a vacuum oven for 30 minutes at 60° C. Then the same steps enumerated in Example 1 were followed. The melt occurred about 3-5 seconds after contacting the spatula with the hot plate.

The resulting pellet exhibited the same characteristics of the pellet made according to Example 1.

This invention is especially adapted for providing an implant useful for fertility control when implanted under the skin in mammals. A most preferred embodiment is a 35 mg. pellet containing cholesterol and nonethindrone at a ratio of about 15:85%. The pellet most preferably is approximately 2½ millimeters in diameter by 6 millimeters in length.

It should be understood that various changes and modifications of the embodiments described may be made within the scope of this invention. Applicant has described a pellet having a particular size. Other sizes and various shapes are contemplated by this invention. Applicant has described only a particular active ingredient, nonethindrone, and a particular lipoid carrier, cholesterol. Other active ingredients and carriers are contemplated by the invention. For example, cholesteric esters such as cholesterol chloride or cholesterol acetate may be substituted for pure cholesterol and lipoid carriers other than cholesterol possibly may be suitable. Likewise, steroids other than nonethindrone and possibly drugs other than steroids may be substituted. Thus, it is intended that all matter contained in the above-description or shown in the accompanying drawings shall be interpreted in an illustrative and not limiting sense.

What is claimed is:

1. A process for preparing a fused pellet from pelleting material comprising,
    forming a thin layer of said material on a surface of a heat conductive base,
    orienting said thin layer and said base at an inclined angle,
    applying heat to the opposite surface of said base sufficient to cause said material to melt uniformly,
    collecting said melted material as it beads upon and runs from said inclined surface, and
    allowing said collected material to cool into a fused pellet.

2. A process as claimed in claim 1 wherein said surface upon which said thin layer is coated is a nonstick surface.

3. A process as claimed in claim 2 wherein said nonstick surface is a Teflon ®-coated surface.

4. A process as claimed in claim 2 further comprising mixing a steroid with a cholesterol ester to form said pelleting material.

5. A process as claimed in claim 4 wherein said cholesterol ester is selected from the group consisting of cholesterol, cholesterol acetate and cholesterol chloride.

6. A process as claimed in claim 2 wherein said thin layer of material is prepared by forming a paste,
    forming a paste of said material,
    spreading said paste of material on said surface, and
    allowing said paste to dry.

7. A process as claimed in claim 2 further comprising the steps of drawing a predetermined amount of said collected material with a plunger into a tableting chamber prior to said material cooling.

8. A process as claimed in claim 2 further comprising the steps of applying a vacuum to said material as it is collected.

9. A process for preparing a fused pellet from pelleting material including at least one pharmaceutical agent comprising,
    applying conditions to said material to melt said material uniformly such that the phase transition of all of said material occurs approximately simultaneously,
    removing said material from said melting conditions immediately upon the melting of said material, and allowing said melted material to cool.

10. A process as claimed in claim 9 further comprising mixing a steroid and a lipoid carrier to form said pelleting material.

11. A process as claimed in claim 9 wherein said conditions cause said material to melt within 10 seconds after the application of melting conditions.

12. A process as claimed in claim 11 wherein said conditions cause said material to melt within about 5 seconds after the application of melting conditions.

13. A method for preparing a fused implant for fertility control comprising,
    forming a finely-divided mixture of anti-ovulation sex hormone and a pure lipoid carrier, said sex hormone present in an amount of at least 50% of said total mixture,
    forming a thin layer of said mixture on a first surface of a heat conductive base,
    orienting said thin layer and said first surface at an inclined angle,
    applying heat in excess of the melting temperature of said hormone and carrier to a second opposite surface of said heat conductive base, said temperature being sufficiently high to cause said mixture to melt uniformly,
    removing said material immediately upon it reaching the melted phase, collecting said melted material as it beads and runs off of said inclined surface, and
    subjecting said collected mixture to cooling conditions.

14. A process as claimed in claim 13 wherein said surface upon which said thin layer is coated is a nonstick surface.

15. A process as claimed in claim 14 wherein said nonstick surface is a Teflon ®-coated surface.

16. A process as claimed in claim 13 wherein said thin layer of material is formed on said surface by,
    forming a paste of said material, spreading said paste of material on said surface, and allowing said paste to dry.

17. A process as claimed in claim 13 further comprising mixing a steroid with a cholesterol ester to form said pelleting material.

18. A process as claimed in claim 13 further comprising the steps of drawing a predetermined amount of said collected material with a plunger into a pelleting chamber prior to said material cooling.

19. A process for forming a implantable pellet containing an active ingredient and a carrier present in precise relative amounts, said active ingredient present in an amount of at least 50% of the total material in said tablet, comprising,
dispensing a first amount of said active ingredient,
dispensing a second amount of said carrier,
mixing said first and second amounts with a liquid to form a predetermined amount of said paste, applying conditions to said paste to cause said paste to melt,
collecting said melted material, and,
allowing said melted material to cool.

20. A process for preparing a fused pellet from a pharmaceutical agent and a carrier having a lower melting temperature than said pharmaceutical agent comprising,
mixing said carrier and said pharmaceutical agent to form pelleting material,
applying conditions to said pelleting material to melt the carrier uniformly such that the phase transition of all of the carrier occurs approximately simultaneously, and the pharmaceutical agent remains as a solid dispersed throughout said melted carrier,
removing said material from said melting conditions immediately upon the melting of said carrier, and allowing said material to cool.

* * * * *

UNITED STATES PATENT AND TRADEMARK OFFICE
CERTIFICATE OF CORRECTION

PATENT NO. : 4,748,024
DATED : May 31, 1988
INVENTOR(S) : Robert J. Leonard

It is certified that error appears in the above-identified patent and that said Letters Patent is hereby corrected as shown below:

Column 4, line 17, please change "nonethindrone" to --norethindrone--.
Column 8, line 55, please change "nonethindrone" to --norethindrone--.
Column 9, line 7, please change "nonethindrone" to --norethindrone--.
Column 9, line 18, please change "nonethindrone" to --norethindrone--.
Column 9, line 31, please change "nonethindrone" to --norethindrone--.
Column 9, line 41, please change "nonethindrone" to --norethindrone--.
Column 9, line 47, please change "nonethindrone" to --norethindrone--.

In the ABSTRACT, line 2, please change "nonethindrone" to "norethindrone--.

Signed and Sealed this

Eighth Day of November, 1988

*Attest:*

DONALD J. QUIGG

*Attesting Officer*  *Commissioner of Patents and Trademarks*